US008598172B2

(12) United States Patent
Caruso et al.

(10) Patent No.: US 8,598,172 B2
(45) Date of Patent: Dec. 3, 2013

(54) SUBSTITUTED DIHYDROPTERIDIN-6-ONE DERIVATIVES, PROCESS FOR THEIR PREPARATION AND THEIR USE AS KINASE INHIBITORS

(75) Inventors: Michele Caruso, Milan (IT); Italo Beria, Nerviano (IT); Maria Gabriella Brasca, Cusago (IT); Helena Posteri, Travedona Monate (IT); Gabriele Fachin, Cilavegna (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 470 days.

(21) Appl. No.: 12/744,770

(22) PCT Filed: Nov. 26, 2008

(86) PCT No.: PCT/EP2008/066253
§ 371 (c)(1),
(2), (4) Date: Jun. 8, 2010

(87) PCT Pub. No.: WO2009/071480
PCT Pub. Date: Jun. 11, 2009

(65) Prior Publication Data
US 2011/0053944 A1    Mar. 3, 2011

(30) Foreign Application Priority Data
Dec. 4, 2007  (EP) .................................... 07122297

(51) Int. Cl.
*A61K 31/495*  (2006.01)
*C07D 475/00*  (2006.01)
(52) U.S. Cl.
USPC ......................................... 514/249; 544/258
(58) Field of Classification Search
USPC ........................................... 544/258; 514/249
See application file for complete search history.

(56) References Cited

U.S. PATENT DOCUMENTS

2004/0029885 A1* 2/2004 Bauer et al. ................... 514/251

FOREIGN PATENT DOCUMENTS

| WO | WO 01/19825 A1 | 3/2001 |
| WO | WO 03/020722 A1 | 3/2003 |
| WO | WO 2004/076054 A2 | 9/2004 |
| WO | WO 2004/076454 A1 | 9/2004 |
| WO | WO 2004/080980 A1 | 9/2004 |
| WO | WO 2006/021548 A1 | 3/2006 |
| WO | WO 2007/090844 A1 | 8/2007 |
| WO | WO 2007/095188 A2 | 8/2007 |

OTHER PUBLICATIONS

Steegmaier M. et al., "BI 2536, a Potent and Selective Inhibitor of Polo-Like Kinase 1, Inhibits Tumor Growth In Vivo", *Current Biology* 17(4):316-322 (2007).

Van Vugt M. et al., "Getting in and Out of Mitosis with Polo-Like Kinase-1", *Oncogene* 2(17)4:2844-2859 (2005).
Barr F.A. et al., "Polo-Like Kinases and the Orchestration of Cell Division", *Nature Reviews Molecular Biology* 5(6):429-440 (2004).
Dai W. et al., "Polo-Like Kinases and the Microtubule Organization Center: Targets for Cancer Therapies", *Progress in Cell Cycle Research* 5:327-334 (2003).
Glover D.M. et al., "Polo-Like Kinases: a Team that Plays Throughout Mitosis", *Genes and Development* 12(24):3777-3787 (1998).
Inoue D. et al., "The Polo-Like Kinase Plx1 Interacts with and Inhibits Myt1 After Fertilization of *Xenopus* Eggs", *The EMBO Journal* 24(5):1057-1067 (2005).
Van Vugt M. et al., "Polo-Like Kinase-1 is Required for Bipolar Spindle Formation but is Dispensable for Anaphase Promoting Complex/Cdc20 Activation and Initiation of Cytokinesis", *The Journal of Biological Chemistry* 279(35):36841-36854 (2004).
Watanabe N. et al., "M-Phase Kinases Induce Phospho-Dependent Ubiquitination of Somatic Wee1 by $SCF^{\beta-TrCP}$", *PNAS* 101(13):4419-4424 (2004).
Nakajima H. et al., "Identification of a Consensus Motif for Plk (Polo-Like Kinase) Phosphorylation Reveals Myt1 as a Plk1 Substrate", *The Journal of Biological Chemistry* 278(28):25277-25280 (2003).
Taniguchi E. et al., "Nuclear Translocation of Plk1 Mediated by Its Bipartite Nuclear Localization Signal", *The Journal of Biological Chemistry* 277(50):48884-48888 (2002).
Bartholomew C.R. et al., "Cdc5 Interacts with the Wee1 Kinase in Budding Yeast", *Molecular and Cellular Biology* 21(15):4949-4959 (2001).
Qian Y-W et al., "The Polo-Like Kinase Plx1 is Required for Activation of the Phosphatase Cdc25C and Cyclin B-Cdc2 in *Xenopus* Oocytes", *Molecular Biology of the Cell* 12(6):1791-1799 (2001).
Roshak A.K. et al., "The Human Polo-Like Kinase, PLK, Regulates Cdc2/Cyclin B Through Phosphorylation and Activation of the Cdc25C Phosphatase", *Cellular Signalling* 12(6):405-411 (2000).
Syed N. et al., "Transcriptional Silencing of Polo-Like Kinase 2 (*SNK/PLK2*) is a Frequent Event in B-Cell Malignancies", *Blood* 107(1):250-256 (2006).
Pak D.T.S. et al., "Targeted Protein Degradation and Synapse Remodeling by an Inducible Protein Kinase", *Science* 302:1368-1373 (2003).
Kauselmann G. et al., "The Polo-Like Protein Kinases Fnk and Snk Associate with a $Ca^{2+}$- and Integrin-Binding Protein and are Regulated Dynamically with Synaptic Plasticity", *The EMBO Journal* 18(20):5528-5539 (1999).
Search Report dated Sep. 2, 2009 received from the European Patent Office.

* cited by examiner

*Primary Examiner* — Shengjun Wang
(74) *Attorney, Agent, or Firm* — Scully, Scott, Murphy & Presser, P.C.

(57) ABSTRACT

Dihydropteridin-6-one derivatives of formula (I) as defined in the specification, and pharmaceutically acceptable salts thereof, process for their preparation and pharmaceutical compositions comprising them are disclosed; the compounds of the invention may be useful, in therapy, in the treatment of diseases associated with a disregulated protein kinase activity, like cancer.

12 Claims, No Drawings

SEQUENCE LISTING

```
<160> NUMBER OF SEQ ID NOS: 6

<210> SEQ ID NO 1
<211> LENGTH: 82
<212> TYPE: DNA
<213> ORGANISM: Artificial
<220> FEATURE:
<223> OTHER INFORMATION: Forward primer

<400> SEQUENCE: 1
ggggacaagt ttgtacaaaa aagcaggctt attcgaaaac ctgtattttc agggccctag      60
tgctgcagtg actgcaggga ag                                              82

<210> SEQ ID NO 2
<211> LENGTH: 60
<212> TYPE: DNA
<213> ORGANISM: Artificial
<220> FEATURE:
<223> OTHER INFORMATION: Reverse primer

<400> SEQUENCE: 2
ggggaccact ttgtacaaga aagctgggtt tcactattta ttgaggactg tgagggctt       60

<210> SEQ ID NO 3
<211> LENGTH: 80
<212> TYPE: DNA
<213> ORGANISM: Artificial
<220> FEATURE:
```

```
<223> OTHER INFORMATION: Forward primer

<400> SEQUENCE: 3
ggggacaagt tgtacaaaa aagcaggctt actggaagtt ctgttccagg ggcccgagct    60
tttgcggagc atcacctacc                                              80

<210> SEQ ID NO 4
<211> LENGTH: 60
<212> TYPE: DNA
<213> ORGANISM: Artificial
<220> FEATURE:
<223> OTHER INFORMATION: Reverse primer

<400> SEQUENCE: 4
ggggaccact tgtacaaga aagctgggtt ttatttgcca ccaaaaagag cagcagctgc    60

<210> SEQ ID NO 5
<211> LENGTH: 83
<212> TYPE: DNA
<213> ORGANISM: Artificial
<220> FEATURE:
<223> OTHER INFORMATION: Forward primer

<400> SEQUENCE: 5
ggggacaagt tgtacaaaa aagcaggctt actggaagtt ctgttccagg ggcccgagcc    60
tgccgccggt ttcctgtctc cgc                                          83

<210> SEQ ID NO 6
<211> LENGTH: 66
<212> TYPE: DNA
<213> ORGANISM: Artificial
<220> FEATURE:
<223> OTHER INFORMATION: Reverse primer

<400> SEQUENCE: 6
ggggaccact tgtacaaga aagctgggtt ttactttctg acaaagaggc tcttggtaac    60
tttggc                                                             66
```

SUBSTITUTED DIHYDROPTERIDIN-6-ONE DERIVATIVES, PROCESS FOR THEIR PREPARATION AND THEIR USE AS KINASE INHIBITORS

The present invention relates to certain substituted dihydropteridin-6-one compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The use of mitotic inhibitors in cancer therapy is a widely accepted clinical strategy for the treatment of a broad range of human cancers. Taxanes (Paclitaxel and Docetaxel) and Vinca Alkaloids (Vincristine and Vinblastine) work by either stabilizing or destabilizing microtubules with catastrophic consequences in cells progressing through mitosis. They are first line therapeutics for several tumour types and second line in cisplatin-refractory ovarian, breast, lung, bladder and esophagus cancers (Taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types. Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle. These checkpoints often go away during oncogenic transformation and this permits cancer cells to tolerate anueploidy and chromosomal instability Inhibition of mitosis in "checkpoint compromised" tumour cells should have catastrophic consequences as cancer cells try to carry forward an aberrant mitosis.

The Polo-like kinase family, comprising 4 serine/threonine kinases (Plk-1-4), are predominantly involved in the entry into, progression through and exit from mitosis. These kinases are characterized by having an n-terminal kinase domain and a unique, c-terminal, "Polo-Box" domain. This domain is responsible for targeting the kinase to various mitotic structures (centrosomes, kinetochores, spindle poles, midbody) and the temporal and spatial regulation of Plks are important for normal progression through mitosis (reviewed in van Vugt and Medema, Oncogene 2005, 24(17):2844-59; Barr et al, Nat Rev Mol Cell Biol. 2004, 5(6):429-40; Dai and Cogswell, Prog Cell Cycle Res. 2003, 5:327-34; Glover et al, Genes Dev. 1998, 12(24):3777-87). The most characterized member of the family is Plk-1 and its enzymatic activity has been implicated in several processes during mitosis including the G2/M transition, centrosome maturation and separation, regulation of chromosomal-arm cohesion at prophase and sister chromatid separation at metaphase/anaphase transition, activation of the Anaphase Promoting Complex to start mitotic exit, cytokinesis (Inoue et al, EMBO J. 2005, 24(5): 1057-67; van Vugt et al, J Biol. Chem. 2004, 9(35):36841-54; Watanabe et al, Proc Natl Acad Sci USA. 2004, 101(13): 4419-24 2004; Nakajima et al, J Biol. Chem. 2003, 278(28): 25277-80; Toyoshima-Morimoto et al, J Biol. Chem. 2002, 277(50):48884-8; Bartholomew et al, Mol Cell Biol., 2001 21(15):4949-59; Qian et al, Mol Biol Cell. 2001, 12(6):1791-9; Roshak et al, Cell Signal. 2000, 12(6):405-11). Plk-1 is over-expressed in several tumour cells including breast, ovarian, non small cell lung, colon, head and neck, endometrial and esophageal carcinomas and its over-expression often correlates with poor prognosis.

Disruption of Plk-1 function by various means in tumoural cells (siRNA and antisense ablation, dominant negative proteins and immunodepletion) results in an aberrant mitosis followed by mitotic catastrophe whilst causing a "checkpoint-mediated" cell cycle arrest in normal cells. Thus, pharmacological attenuation of Plk-1 function may have a therapeutic benefit in the treatment of several diverse cancers.

Inhibition of PLK1 is sufficient to cause mitotic block in the cell cycle and apoptosis, while inhibition of the other two members of the family is not essential for the cell cycle block and moreover could be associated to secondary effects like hematological malignancies or neurotoxicity. As reported in the literature, Plk2 is transcriptionally down-regulated in B-cell neoplasms. Silencing occurs with very high frequency in Burkitt lymphoma (BL) but is also detected in B-cell neoplasms of other types and is associated with aberrant cytosine methylation. Ectopic expression of Snk/Plk2 in BL cells resulted in apoptosis indicating a possible role of PLK2 as tumor suppressor in B cell neoplasia (Syed, N. et al. *Blood* 2006, 107, 250-256). Moreover both PLK2 and PLK3 have been reported to play important nonmitotic roles in neuronal synaptic plasticity (Pak, D. T. *Science* 2003, 302, 1386-1373; Kauselmann, G. *EMBO J.* 1999, 18, 5528-5539).

Pteridinone derivatives for the treatment of cell proliferative disorders such as cancer, are disclosed in WO 2001/019825 in the name of Warner Lambert Co.

Dihydropteridin-6-one derivatives and their salts for the treatment of cell proliferative disorders are also disclosed in WO 2003/020722, WO2004/076054 and WO2007/090844 all in the name of Boehringer Ingelheim Pharma.

Despite these developments, there is still need for effective agents for said disorders. The present inventors have now discovered that compounds of formula (I), described below, are selective PLK1 inhibitors and are thus useful in therapy as antitumor agents and lack, in terms of both toxicity and side effects, the aforementioned drawbacks associated with currently available antitumor drugs.

Accordingly, a first object of the present invention is to provide a substituted dihydropteridin-6-one compound represented by formula (I):

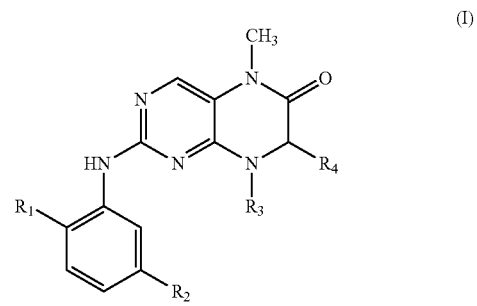

wherein $R_1$ is an optionally substituted group selected from straight or branched $C_1$-$C_3$ alkyl, $C_1$-$C_3$ alkoxy, $C_1$-$C_3$ polyfluorinated alkyl, $C_1$-$C_3$ polyfluorinated alkoxy and —COR', wherein R' is an optionally substituted $C_1$-$C_6$ alkyl;

$R_2$ is a —NR"R'" group, wherein R" and R'" are, each independently, hydrogen or an optionally substituted group selected from straight or branched $C_1$-$C_6$ alkyl, $C_3$-$C_6$ cycloalkyl and heterocyclyl or taken together with the nitrogen atom to which they are bonded, R" and R'" may form an optionally substituted heterocyclyl ring optionally containing one additional heteroatom selected from N, O or S;

$R_3$ and $R_4$ are, each independently, hydrogen or an optionally substituted group selected from straight or branched $C_1$-$C_6$ alkyl, $C_3$-$C_6$ cycloalkyl and heterocyclyl, and pharmaceutically acceptable salts thereof.

The present invention also provides methods of synthesizing the substituted dihydropteridin-6-one compounds, represented by formula (I), prepared through a process consisting of standard synthetic transformations.

The present invention also provides a method for treating diseases caused by and/or associated with dysregulated protein kinase activity, particularly PLK family, ABL, AKT1, ALK, AUR1, AUR2, BRK, CDC7/$DBF_4$, CDK2/CYCA, CHK1, CK2, EGFR1, ERK2, FAK, FGFR1, FLT3, GSK3beta, IGFR1, IKK2, IR, JAK2, JAK3, KIT, LCK, MAPKAPK2, MET, MPS1, NEK6, NIM1, P38alpha, PAK4, PDGFR, PDK1, PIM1, PKAalpha, PKCbeta, PLK1, RET, STLK2, SULU1, TRKA, VEGFR2, VEGFR3, ZAP70, more particularly the compound have shown a selective activity versus PLK1 kinase respect to PLK2 and PLK3.

A preferred method of the present invention is to treat a disease caused by and/or associated with dysregulated protein kinase activity selected from the group consisting of cancer, cell proliferative disorders, autoimmune and neurodegenerative disorders. Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The present invention further provides a method of treatment comprising a compound of formula (I) in combination with radiation therapy or chemotherapy regimen for simultaneous, separate or sequential use in anticancer therapy.

Moreover the invention provides a method for inhibiting PLK-1 protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament. Moreover, the invention provides a compound of formula (I) or a pharmaceutically acceptable salt thereof, as defined above, for use in a method of treating cancer.

Finally the invention provides the use of a compound of formula (I) or a pharmaceutically acceptable salt thereof, as defined above, in the manufacture of a medicament with antitumor activity.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

In the present description, with the term "straight or branched alkyl" we intend, unless otherwise specified, $C_1$-$C_6$ alkyl groups and $C_1$-$C_3$ alkyl groups which are alkyl group having respectively from 1 to 6 and from 1 to 3 carbon atoms, such as, for instance, methyl, ethyl, n-propyl, isopropyl, n-butyl, isobutyl, tert-butyl, sec-butyl, n-pentyl, n-hexyl, and the like.

With the term $C_1$-$C_3$ alkoxy, we intend any of the above $C_1$-$C_3$ alkyl groups linked to the rest of the molecule through a oxygen atom (—O—).

With the term $C_1$-$C_3$ polyfluorinated alkyl or alkoxy we intend any of the above straight or branched $C_1$-$C_3$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "$C_3$-$C_6$ cycloalkyl" we intend, unless otherwise specified, 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocycloalkyl groups are, for instance, pyrane, pyrrolidine, pyrroline, imidazo line, imidazolidine, pyrazolidine, pyrazoline, thiazoline, thiazolidine, dihydrofuran, tetrahydrofuran, 1,3-dioxo lane, piperidine, piperazine, morpholine and the like. Whenever appropriate, each of the above substituent may be further substituted by one or more of the aforementioned groups.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt. Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:
$R_4$ is an optionally substituted straight or branched $C_1$-$C_6$ alkyl.

A further preferred class of compounds of formula (I) are the compounds wherein:
$R_1$ is a group selected from —$OCF_3$, —$OCH_3$, —$CH_3$ and —COR', wherein R' is as defined above;
$R_2$ is methylpiperazinyl group

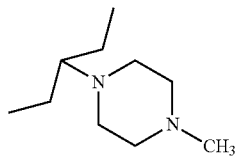

and $R_3$ is $C_3$-$C_6$ cycloalkyl.

Particularly preferred compounds of formula (I) are the compounds listed below:
(R)-8-Cyclopentyl-7-ethyl-5-methyl-2-[5-(4-methyl-piperazin-1-yl)-2-trifluoromethoxy-phenylamino]-7,8-dihydro-5H-pteridin-6-one,
(R)-8-Cyclopentyl-7-ethyl-2-[2-methoxy-5-(4-methyl-piperazin-1-yl)-phenylamino]-5-methyl-7,8-dihydro-5H-pteridin-6-one and
(R)-8-Cyclopentyl-7-ethyl-5-methyl-2-[2-methyl-5-(4-methyl-piperazin-1-yl)-phenylamino]-7,8-dihydro-5H-pteridin-6-one.

For a reference to any specific compound of formula (I) of the invention, optionally in the form of a pharmaceutically acceptable salt, see the experimental section and claims.

The present inventions also provides a process for the preparation of compounds of formula (I) as defined above, characterized in that the process comprises:
st.1) reacting the compound of formula (II):

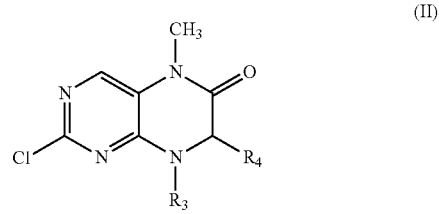

wherein $R_3$ and $R_4$ are as defined above, with a compound of formula (III):

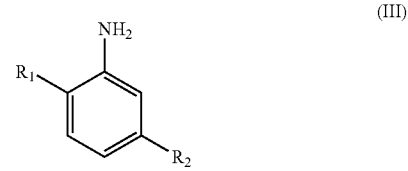

wherein $R_1$ and $R_2$ are as defined above, to give a compound of formula (I) and optionally converting it into pharmaceutically acceptable salts thereof.

The above process is an analogy process and can be carried out according to methods well known in the art.

According to step 1 (st1) of the process, the reaction of the compound of formula (II) with the compound of formula (III) can be accomplished in a variety of ways according to conventional methods. Preferably it is carried out in a suitable solvent such as ethanol or water or a mixture of them, in acidic conditions e.g HCl, at a temperature ranging from room temperature to about 100° C. and for a time of about 2 to about 48 hours. According to any variant of the process for preparing the compounds of formula (I), the starting materials and any other reactants are known or easily prepared according to known methods. The compounds of formula (II) can be prepared as described in WO2003/020722 and WO 2004/076454. Some compounds of formula (III) are commercially available, others can be analogously prepared as described in the following preparations 2 to 4.

From all of the above, it is clear to the skilled person that when preparing the compounds of formula (I) according to the aforementioned process, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of formula (I) prepared according to the process described above are obtained as mixture of isomers, their separation using conventional techniques into the single isomers of formula (I), or conventional techniques for racemate resolution include, for instance, partitioned crystallization of diastereoisomeric salt derivatives or preparative chiral HPLC is within the scope of the present invention. Conventional techniques for racemate resolution include, for instance, partitioned crystallization of diastereoisomeric salt derivatives or preparative chiral HPLC.

Pharmacology

The compounds of formula (I) are active as protein kinase inhibitors and are therefore useful, for instance, to restrict the unregulated proliferation of tumor cells.

In therapy, they may be used in the treatment of various tumors, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The inhibiting activity of putative PLK-1 inhibitors and the potency of selected compounds was determined through the assay described below.

The short forms and abbreviations used herein have the following meaning:

| | |
|---|---|
| Ci | Curie |
| DMSO | dimethylsulfoxide |
| KDa | kiloDalton |
| microCi | microCurie |
| mg | milligram |
| microg | microgram |
| ng | nanogram |
| L | liter |
| mL | milliliter |
| microL | microliter |
| M | molar |
| mM | millimolar |
| microM | micromolar |
| nM | nanomolar |
| Et | ethyl |

Cloning, Expression and Purification of Recombinant PLK1 Kinase Domain.

PLK1 kinase domain (corresponding to residues 2-345 of the full length sequence, see Swiss-Prot accession number P53350) was PCR amplified from the full-length human PLK1 gene purchased from imaGenes as clone IRATp970A078D.

Amplification was performed using the forward oligonucleotide:

[SEQ ID NO: 1]
5'GGGGACAAGTTTGTACAAAAAAGCAGGCTTATTCGAAAACCTGTA
TTTTCAGGGCCCTAGTGCTGCAGTGACTGCAGGGAAG3' and the reverse oligonucleotide:

[SEQ ID NO: 2]
5'GGGGACCACTTTGTACAAGAAAGCTGGGTTTCACTATTTATTGAG
GACTGTGAGGGGCTT-3'.

For cloning purposes, the oligonucleotides included attB sites in order to obtain an attB-flanked PCR product suitable for cloning using the Gateway® technology (Invitrogen). Furthermore, for purification purposes, forward primer included a TEV® cleavage site (Amersham Biosciences). The resulting PCR product was cloned in the pDONR221 plasmid and then transferred in the baculovirus expression vector pVL1393 (Invitrogen) Gateway®-modified. For expression and purification purposes, a His tag was added N-terminal to the PLK kinase domain. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 48 hours of infection, cells were recovered, pelletted and freezed at −80° C. For purification of recombinant protein, pellet was thawed, resuspended in lysis buffer (PBS, NaCl 150 mM, CHAPS 0.1%, DTT 20 mM, glycerol 10%, protease inhibitors) and lysed by sonication. Lysate was cleared by centrifugation and loaded on a Nichel affinity column. After extensive wash, recombinant protein was cleaved and eluted by incubation with TEV® protease.

Biochemical Assay for Inhibitors of PLK-1 Kinase Activity

The inhibitory activity of putative kinase inhibitors and the potency of selected compounds were determined using a trans-phosphorylation assay.

Specific peptide or protein substrates are trans-phosphorylated by their specific serine-threonine or tyrosine kinase, in the presence of ATP traced with $^{33}$P-γ-ATP, and in the presence of their own optimal buffer and cofactors.

At the end of the phosphorylation reaction, more than 98% cold ATP and radioactive ATP is captured by an excess of the ion exchange dowex resin; the resin then settles down to the bottom of the reaction plate by gravity.

Supernatant, containing the phosphorylated substrate, is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded. After three washes as above over a couple of days, the resin is allowed to settle, the supernatant is discarded and two volumes of 150 mM sodium formate buffer are added per volume of pellet. The pH is then measured and should be around 3.00. The washed resin is stable for more than one week; the stock resin is kept at 4° C. before use.

ii. Kinase Buffer (KB)

Kinase buffer for PLK1 assay was composed of 50 mM HEPES pH 7.9 containing 10 mM MgCl$_2$, 1 mM DTT, 3 microM NaVO$_3$, and 0.2 mg/mL BSA, 10 mM β-glycerophosphate.

iii Assay Conditions

The kinase assay was run with a final enzyme concentration PLK-1 of 3 nM, in presence of 40 microM ATP, 3 nM $^{33}$P-γ-ATP and 85 microM substrate alpha-casein, SIGMA, # C-3240.

Robotized Dowex Assay 1) 3× Enzyme mix (done in Kinase Buffer 3×), 5 microL/well
2) 3× substrate and ATP mix (done in ddH$_2$O), together with $^{33}$P-γ-ATP, 5 microL/well
3) 3× test compounds (diluted into ddH$_2$O—3% DMSO)—5 microL/well Compound Dilution and Assay Scheme is Defined Below.

i. Dilution of compounds 10 mM stock solutions of test compounds in 100% DMSO were distributed into 96 well 12×8 format microtiter plates.

For % inhibition studies, individual dilution plates at 1 mM, 100 microM and 10 microM are prepared in 100% DMSO, then diluted at a 3× concentration (30, 3 and 0.3 microM) in ddH$_2$O, 3% DMSO. A Multimek 96 (Beckman) is used for dilutions and compound pipetting into the test plates For IC$_{50}$ determination, compounds are received as 1 mM, 100% DMSO solutions, plated into the first column of a microtiter plate (A1 to G1), 100 microL.

A Biomek 2000 (Beckman) is used for serial 1:3 dilutions in water, 3% DMSO, from column A1 to A10 and for all the seven compounds in the plate. In a standard experiment, the highest concentration of all compounds is 30 microM, then diluted in the final test mixture down to 10 microM.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×). At the start of the run, the robot aspirates 5 microL of ATP mix, makes an air gap inside the tips (3 microL) and aspirates 5 microL of PLK1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

Another mixing cycle is performed after all the plates are stopped, this time using normal tips: the plates are then allowed to rest for about one hour in order to maximize ATP capture. At this point, 20 microL of the supernatant are transferred into 384-Optiplates (Perkin-Elmer), with 70 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for IC$_{50}$ determination, for the secondary assays/hit confirmation routines.

Cloning, Expression and Purification of Recombinant PLK2 Kinase Domain.

PLK2 Kinase domain (corresponding to residues 2-375 of the full length sequence, see Swiss-Prot accession number Q9NYY3) was PCR amplified from a human testis cDNA library. Amplification was performed using the forward oligonucleotide:

```
                                          [SEQ ID NO: 3]
5'GGGGACAAGTTTGTACAAAAAAGCAGGCTTACTGGAAGTTCTGT

TCCAGGGGCCCGAGCTTTTGCGGAGCATCACCTACC-3'
``` and the reverse oligonucleotide:

```
                                          [SEQ ID NO: 4]
5'GGGGACCACTTTGTACAAGAAAGCTGGGTTTTATTTGCCACCAA

AAAGAGCAGCAGCTGC-3'.
```

For cloning purposes, the oligonucleotides included attB sites in order to obtain an attB-flanked PCR product suitable for cloning using the Gateway® technology (Invitrogen). Furthermore, for purification purposes, forward primer included a PreScission® cleavage site (Amersham Biosciences). The resulting PCR product was cloned in the baculovirus expression vector pVL1393 (Invitrogen) Gateway®-modified. For expression and purification purposes, a GST tag was added N-terminal to both PLKs kinase domains. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatants were recovered after 5 days and subjected to 3 rounds of amplification to increase viral titer. Recombinant proteins were produced by infecting High5 insect cells at the density of 1×106 cells per ml with 3 ml viral supernatant per billion cells. After 48 hours of infection, cells were recovered, pelletted and freezed at −80° C. For purification of recombinant proteins, pellets were thawed, resuspended in lysis buffer (Tris-HCl pH7.4 50 mM, NaCl 150 mM, CHAPS 0.2%, DTT 20 mM, glycerol 10%) and lysed by sonication. Lysates were cleared by centrifugation at 24000 g for 30 minutes and loaded on a Glutathione Sepharose 4FF® (Amersham Biosciences) column. After extensive wash, recombinant proteins were cleaved and eluted by incubation with PreScission® protease.

Biochemical Assay for Inhibitors of PLK-2 Kinase Activity

The in vitro kinase inhibition assay was conducted in the same way as described for PLK-1 enzyme.

i. Kinase Buffer (KB) for PLK-2

The kinase buffer was composed of 50 mM HEPES, pH 7.9, 5 mM MgCl$_2$, 1 mM DTT, 3 microM NaVO$_3$, 10 mM β-Glycerophosphate and 0.2 mg/mL BSA.

ii. Assay Conditions for PLK-2 (Final Concentrations)

The kinase assay was run with an enzyme concentration of 5 nM, 200 microM ATP, 3 nM $^{33}$P-γ-ATP, and 175 microM substrate alpha-casein, SIGMA, # C-3240.

Cloning, Expression and Purification of Recombinant PLK3 Kinase Domain.

PLK3 Kinase domain (corresponding to residues 2-355 of the full length sequence, see Swiss-Prot accession number Q9H4B4) was PCR amplified from a human testis cDNA library. Amplification was performed using the forward oligonucleotide:

[SEQ ID NO: 5]
5'GGGGACAAGTTTGTACAAAAAAGCAGGCTTACTGGAAGTTCTGT

TCCAGGGGCCCGAGCCTGCCGCCGGTTTCCTGTCTCCGC-3' and the reverse oligonucleotide:

[SEQ ID NO: 6]
5'GGGGACCACTTTGTACAAGAAAGCTGGGTTTTACTTTCTGACAA

AGAGGCTCTTGGTAACTTTGGC-3'

For cloning purposes, the oligonucleotides included attB sites in order to obtain an attB-flanked PCR product suitable for cloning using the Gateway® technology (Invitrogen). Furthermore, for purification purposes, forward primer included a PreScission® cleavage site (Amersham Biosciences). The resulting PCR product was cloned in the baculovirus expression vector pVL1393 (Invitrogen) Gateway®-modified. For expression and purification purposes, a GST tag was added N-terminal to PLK3 kinase domain. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatants were recovered after 5 days and subjected to 3 rounds of amplification to increase viral titer. Recombinant protein was produced by infecting High5 insect cells at the density of 1×106 cells per ml with 3 ml viral supernatant per billion cells. After 48 hours of infection, cells were recovered, pelletted and freezed at −80° C. For purification of recombinant protein, pellet was thawed, resuspended in lysis buffer (Tris-HCl pH7.4 50 mM, NaCl 150 mM, CHAPS 0.2%, DTT 20 mM, glycerol 10%) and lysed by sonication. Lysate was cleared by centrifugation at 24000 g for 30 minutes and loaded on a Glutathione Sepharose 4FF® (Amersham Biosciences) column. After extensive wash, recombinant protein was cleaved and eluted by incubation with PreScission® protease.

Biochemical Assay for Inhibitors of PLK-3 Kinase Activity

The in vitro kinase inhibition assay was conducted in the same way as described for PLK-1 enzyme.

i. Kinase Buffer (KB) for PLK-3

The kinase buffer was composed of 50 mM HEPES, pH 7.9, 5 mM MgCl$_2$, 1 mM DTT, 3 microM NaVO$_3$, 10 mM β-Glycerophosphate and 0.2 mg/mL BSA.

ii. Assay Conditions for PLK-3 (Final Concentrations)

The kinase assay was run with an enzyme concentration of 0.5 nM, 50 microM ATP, 3 nM $^{33}$P-γ-ATP, and 110 microM substrate alpha-casein, SIGMA, # C-3240.

Biochemical Assay for Inhibitors of Aurora-2 Kinase Activity

The in vitro kinase inhibition assay was conducted in the same way as described for PLK-1 enzyme.

i. Kinase Buffer (KB) for Aurora-2

The kinase buffer was composed of 50 mM HEPES, pH 7.0, 10 mM MgCl$_2$, 1 mM DTT, 3 microM NaVO$_3$, and 0.2 mg/mL BSA.

ii. Assay Conditions for Aurora-2 (Final Concentrations)

The kinase assay was run with an enzyme concentration of 2.5 nM, 10 microM ATP, 1 nM $^{33}$P-γ-ATP, and 8 microM substrate, composed of 4 LRRWSLG repeats.

Inhibition Assay of Cdk2/Cyclin A Activity

Kinase reaction: 1.5 microM histone H1 substrate, 25 microM ATP (0.2 microCi P33γ-ATP), 30 ng of baculovirus co-expressed Cdk2/Cyclin A, 10 microM inhibitor in a final volume of 100 microL buffer (TRIS HCl 10 mM pH 7.5, MgCl$_2$ 10 mM, 7.5 mM DTT) were added to each well of a 96 U bottom well plate. After 10 min at 37° C. incubation, reaction was stopped by 20 microL EDTA 120 mM.

Capture: 100 microL were transferred from each well to MultiScreen plate, to allow substrate binding to phosphocellulose filter. Plates were then washed 3 times with 150 microL/well PBS Ca$^{++}$/Mg$^{++}$ free and filtered by MultiScreen filtration system.

The in vitro kinase inhibition assay was conducted in the same way as described for PLK-1 enzyme.

i. Kinase Buffer (KB) for CDK-2/CycA

The kinase buffer was composed of TRIS HCl 50 mM pH 7.5, MgCl2 10 mM, DTT 1 mM, NaVO3 3 microM, 0.2 mg/ml BSA ii. Assay Conditions for CDK-2 (Final Concentrations)

The kinase assay was run with an enzyme concentration of 1.08 nM, 10 microM ATP, 1 nM $^{33}$P-γ-ATP, and 4 microM substrate, Histone H1.

In Vitro Cell Proliferation Assay

A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% CO$_2$ and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly 25 microL/well reagent solution are added to each wells and after 5 minutes shacking microplates are red by a luminometer. The luminescent signal is proportional to the number of cells present in culture.

The compounds of formula (I) tested as described above, resulted to possess a remarkable selective PLK1 inhibitory activity in comparison to the isoforms PLK2 and PLK3. In biochemical assays the PLK1 IC$_{50}$ is typically lower than 0.1 microM.

See, as an example, the following table 1 wherein are reported experimental data (IC$_{50}$), tested with the method above, of one representative compound of the invention of formula (I) in comparison with the closest compound of the prior art (Ref.), described in Steegmaier, Martin et al., *Current Biology* 2007, 17(4), 316-322.

TABLE 1

| Compound | PLK1 IC$_{50}$ (microM) | PLK2 IC$_{50}$ (microM) | PLK3 IC$_{50}$ (microM) | PLK2/ PLK1 | PLK3/ PLK1 |
|---|---|---|---|---|---|
| 1 | 0.032 | 1.13 | 1.29 | 35.3 | 40.3 |
| Ref. | 0.008 | 0.03 | 0.09 | 3.7 | 11.2 |

TABLE 1-continued

| Compound | PLK1 IC$_{50}$ (microM) | PLK2 IC$_{50}$ (microM) | PLK3 IC$_{50}$ (microM) | PLK2/ PLK1 | PLK3/ PLK1 |
| --- | --- | --- | --- | --- | --- |

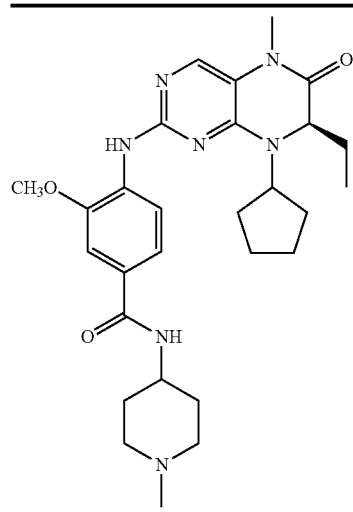

Reference compound (Ref.)

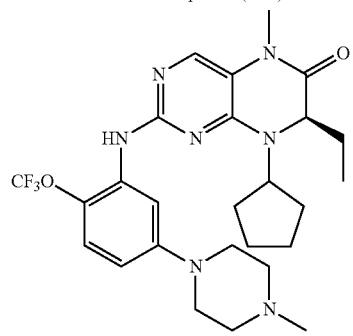

Compound 1

Surprisingly the novel compounds of the present invention resulted to have higher selectivity on PLK1 biochemical assay in comparison with the reference compound. In fact, compounds of formula I of the present have a ratio between PLK2/PLK1 and PLK3/PLK1 higher than that of the reference compound.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

The compounds of the present invention, as prepared according to the following examples, were characterized by $^1$H NMR and by MS analysis.

Example 1

(R)-8-Cyclopentyl-7-ethyl-5-methyl-2-[5-(4-methyl-piperazin-1-yl)-2-trifluoromethoxy-phenylamino]-7,8-dihydro-5H-pteridin-6-one ($R_1$=OCF$_3$, $R_2$=4-methylpiperazine, $R_3$=cyclopentyl, $R_4$=ethyl)

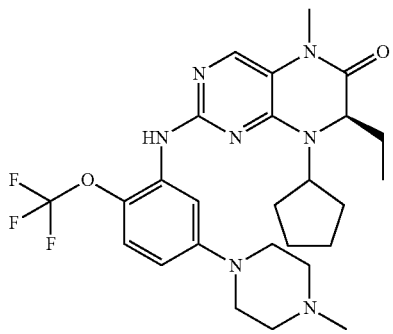 [SMILES: CC[C@@H]1C(=O)N(C)c2cnc(Nc3cc(N4CCN(C)CC4)ccc3OC(F)(F)F)nc2N1C1CCCC1]

To a suspension of (R)-2-Chloro-8-cyclopentyl-7-ethyl-5-methyl-7,8-dihydro-5H-pteridin-6-one (0.60 g, 2 mmol), prepared as described in WO 2004/076454, in a 2/1 mixture H$_2$O/Ethanol (60 mL), were added 37% HCl (0.6 mL) and 2-trifluoromethoxy-5-(4-Methyl-piperazin-1-yl)-phenylamine (0.55 g, 2 mmol), prepared as described in Preparation 1. The reaction was refluxed for 72 hours, concentrated to small volume (20 mL) diluted with water (30 mL) and extracted with DCM (2×50 mL). The aqueous phase was neutralized by addition of NaHCO$_3$ then extracted with DCM (2×50 mL). The organic fractions were combined, dried over sodium sulfate and solvent was evaporated to dryness. Purification of crude solid by flash chromatography on silica gel (eluant: DCM/EtOH 90/10) yield the title compound as an light brown solid (0.23 g, 22% yield).

$^1$H NMR (400 MHz, DMSO-d$_6$) δ ppm 0.76 (t, J=7.50 Hz, 3H) 1.44 (m, 2H) 1.60 (m, 2H) 1.73 (m, 2H) 1.82 (m, 4H) 2.27 (s, 3H) 2.49-2.53 (m, 4H) 3.09-3.18 (m, 4H) 3.23 (s, 3H) 4.18 (dd, J=7.56, 3.66 Hz, 1H) 4.20-4.28 (m, 1H) 6.67 (dd, J=9.15, 3.05 Hz, 1H) 7.12-7.21 (m, 1H) 7.54 (d, J=3.05 Hz, 1H) 7.77 (s, 1H) 7.93 (s, 1H); MS (ESI): 534 [M+H]$^+$.

By analogous procedure and using the suitable starting materials (prepared as described above or in the preparations 2 and 3) the following products can be obtained:

(R)-8-Cyclopentyl-7-ethyl-2-[2-methoxy-5-(4-methyl-piperazin-1-yl)-phenylamino]-5-methyl-7,8-dihydro-5H-pteridin-6-one ($R_1$=OCH$_3$, $R_2$=4-methylpiperazine, $R_3$=cyclopentyl, $R_4$=ethyl)

$^1$H NMR (401 MHz, DMSO-d$_6$) δ ppm 0.78 (t, J=7.44 Hz, 3H) 1.57 (m, 2H) 1.60 (m, 2H) 1.71 (m, 2H) 1.73 (m, 2H) 1.96 (m, 2H) 2.23 (s, 3H) 2.45-2.49 (m, 4H) 3.01 (d, J=5.00 Hz, 4H) 3.25 (s, 3H) 3.80 (s, 3H) 4.18 (dd, J=7.99, 3.72 Hz, 1H) 4.43-4.54 (m, 1H) 6.49 (dd, J=8.78, 2.93 Hz, 1H) 6.88 (d, J=8.90 Hz, 1H) 7.40 (s, 1H) 7.83 (s, 1H) 7.99 (d, J=2.93 Hz, 1H); MS (ESI): 480 [M+H]$^+$.

(R)-8-Cyclopentyl-7-ethyl-5-methyl-2-[2-methyl-5-(4-methyl-piperazin-1-yl)-phenylamino]-7,8-dihydro-5H-pteridin-6-one ($R_1$=CH$_3$, $R_2$=4-methylpiperazine, $R_3$=cyclopentyl, $R_4$=ethyl)

$^1$H NMR (401 MHz, DMSO-d$_6$) δ ppm 0.77 (t, J=7.50 Hz, 3H) 1.41 (m, 2H) 1.58 (m, 2H) 1.71 (m, 2H) 1.74 (m, 2H) 1.83 (m, 2H) 2.11 (s, 3H) 2.22 (s, 3H) 2.41-2.46 (m, 4H) 3.01-3.07 (m, 4H) 3.22 (s, 3H) 4.12 (dd, J=7.80, 3.66 Hz, 1H) 4.18-4.31 (m, 1H) 6.59 (dd, J=8.35, 2.50 Hz, 1H) 7.00 (d, J=8.41 Hz, 1H) 7.16 (d, J=2.56 Hz, 1H) 7.73 (s, 1H) 7.87 (s, 1H); MS (ESI): 464 [M+H]$^+$.

Preparation 1

2-Trifluoromethoxy-5-(4-methyl-piperazin-1-yl)-phenylamine trihydrochloride salt

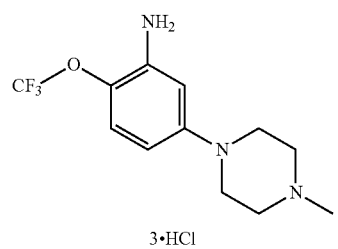 [SMILES: CN1CCN(c2ccc(OC(F)(F)F)c(N)c2)CC1]

Step 1:
N-(5-bromo-2-trifluoromethoxy-phenyl)-acetamide

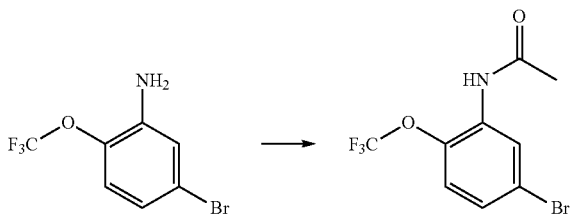 [SMILES: Nc1cc(Br)ccc1OC(F)(F)F ; CC(=O)Nc1cc(Br)ccc1OC(F)(F)F]

To a solution of 2-trifluoromethoxy-5-bromo-phenylamine (5.12 g, 20 mmol) in EtOH (50 mL) at 0° C. was added a solution of acetic anhydride (4.7 mL, 50 mmol) in EtOH (10 mL). The mixture was stirred at room temperature overnight. The solvent was evaporated to dryness and the solid was tritured with diethyl ether and filtered to give 5.64 g (95% yield) of N-(5-bromo-2-trifluoromethoxy-phenyl)-acetamide.

$^1$H NMR (400 MHz, DMSO-d$_6$) δ ppm: 2.11 (s, 3H) 7.39 (m, 2H) 8.21 (s, 1H) 9.87 (s, 1H); MS (ESI): 257 [M+H]$^+$.

Step 2: N-[2-trifluoromethoxy-5-(4-methyl-piperazin-1-yl)-phenyl]-acetamide

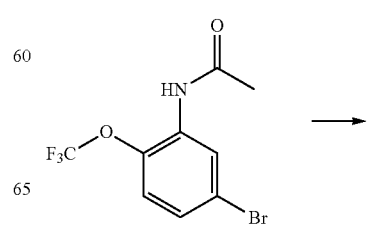

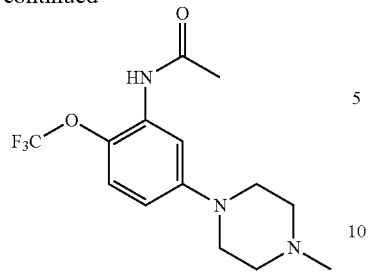

Pd$_2$(dba)$_3$ (157 mg, 0.17 mmol), 2-dicyclohexylphosphino-2'-(N,N-dimethylamino)-biphenyl (134.7 mg, 0.34 mmol), N-(5-bromo-2-trifluoromethoxy-phenyl)-acetamide (5.05 g, 17 mmol)) were charged in a round-bottom flask flushed with argon. The flask was evacuated and backfilled with argon. LiN(TMS)$_2$ solution (1M in THF, 37.6 mL) and N-methylpiperazine (2.3 mL, 20.5 mmol) were added and the reaction mixture refluxed for 3 h. The reaction mixture was then allowed to cool to room temperature and concentrated. The crude solid was purified by flash chromatography on silica gel (eluant: DCM/EtOH 90/10) to afford 4.78 g (88% yield) of the N-[2-trifluoromethoxy-5-(4-methyl-piperazin-1-yl)-phenyl]-acetamide.

$^1$H NMR (400 MHz, DMSO-d$_6$) δ ppm: 2.06 (s, 3H) 2.22 (s, 3H) 2.45 (m, 4H) 3.11 (m, 4H) 6.75 (dd, J=9.15, 3.05 Hz, 1H) 7.17 (dd, J=9.15, 1.46 Hz, 1H) 7.41 (bs, 1H) 9.54 (s, 1H); MS (ESI): 299 [M+H]$^+$.

Step 3: 2-trifluoromethoxy-5-(4-methyl-piperazin-1-yl)-phenylamine trihydrochloride salt

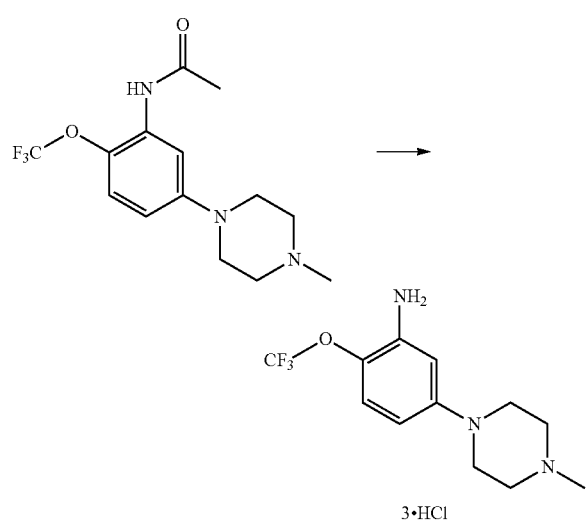

A solution of N-[2-trifluoromethoxy-5-(4-methyl-piperazin-1-yl)-phenyl]-acetamide (4.75 g, 15 mmol) in EtOH (100 mL) was treated with HCl 37% (35 mL). After 1 h under reflux the mixture was concentrated and tritured with hexane to give in quantitative yield, 5.74 g of 2-trifluoromethoxy-5-(4-methyl-piperazin-1-yl)-phenylamine trihydrochloride salt.

$^1$H NMR (400 MHz, DMSO-d$_6$) δ ppm: 2.82 (d, J=4.76 Hz 3H) 3.1 (m, 4H) 3.48 (m, 4H) 6.24 (dd, J=8.90, 2.93 Hz, 1H) 6.40 (d, J=2.93 Hz, 1H) 6.98 (dd, J=8.90, 1.34 Hz, 1H) 10.31 (bs, 1H); MS (ESI): 318 [M+H]$^+$.

Preparation 2

2-Methoxy-5-(4-methyl-piperazin-1-yl)-phenylamine

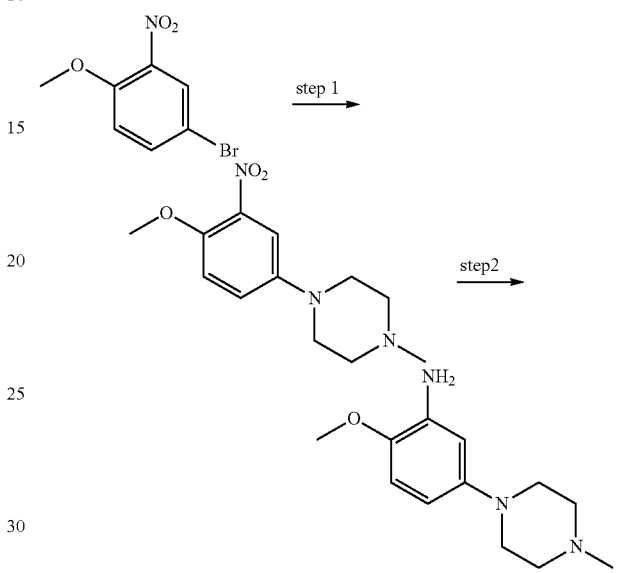

Step 1: 1-(4-methoxy-3-nitro-phenyl)-4-methyl-piperazine

Pd(OAc)$_2$ (85 mg, 0.38 mmol), 2-dicyclohexylphosphino-2'-(N,N-dimethylamino)-biphenyl (225 mg, 0.57 mmol), K$_3$PO$_4$ (2.26 g, 10.68 mmol), 4-bromo-1-methoxy-2-nitrobenzene (1.77 g, 7.63 mmol) in THF (50 mL) were charged in a round-bottom flask flushed with argon. The flask was evacuated and backfilled with argon. N-methylpiperazine (1.01 mL, 9.15 mmol) was added and the reaction mixture was refluxed for 72 h. The reaction mixture was then allowed to cool to room temperature and concentrated. The crude solid was purified by flash chromatography on silica gel (eluant: DCM/EtOH 90/10) to afford 1.05 g (55% yield) of the title compound.

$^1$H NMR (400 MHz, DMSO-d$_6$) δ ppm: 2.22 (s, 3H) 2.45 (m, 4H) 3.09 (m, 4H) 3.83 (s, 3H) 7.22 (d, J=9.27 Hz, 1H) 7.26 (dd, J=9.27 and 2.93 Hz, 1H) 7.35 (d, J=2.93 Hz, 1H).

Step 2: 2-Methoxy-5-(4-methyl-piperazin-1-yl)-phenylamine

A solution of 1-(4-methoxy-3-nitro-phenyl)-4-methyl-piperazine (1.0 g, 4.0 mmol) in MeOH (100 mL) in the presence of Pd/C 10% (150 mg) was hydrogenated at 35 psi for 2 h. The mixture was filtered over a pad of celite and the solution was concentrated to afford 0.8 g (90% yield) of the title compound.

¹H NMR (400 MHz, DMSO-d₆) δ ppm: 2.21 (s, 3H) 2.43 (m, 4H) 2.94 (m, 4H) 3.68 (s, 3H) 4.55 (s, 2H) 6.09 (dd, J=8.66 and 2.80 Hz, 1H) 6.30 (d, J=2.80 Hz, 1H) 6.64 (d, J=8.66 Hz, 1H).

Preparation 3

2-Methyl-5-(4-methyl-piperazin-1-yl)-phenylamine hydrochloride salt

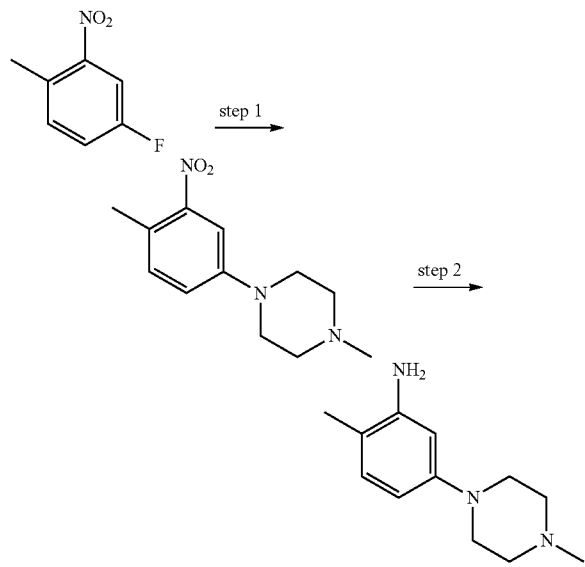

Step 1:
Methyl-4-(4-methyl-3-nitro-phenyl)-piperazine

In a cylindrical quartz tube were placed 4-fluoro-1-methyl-2-nitro-benzene (20.0 g, 129 mmol) and N-methyl-piperazine (26 g, 258 mmol). The reaction was heated for 48 hours at 200° C. until HPLC revealed the disappearance of the starting material. The solvent was removed under reduced pressure and the residue was dissolved in DCM. The solution was washed twice with water and the organic phase was dried over anhydrous Na₂SO₄ and the solvent was removed under reduced pressure. The final compound (14.65 g, 48% yield) was obtained as a brown oil.

Step 2:
2-Methyl-5-(4-methyl-piperazin-1-yl)-phenylamine

To a solution of 1-methyl-4-(4-methyl-3-nitro-phenyl)-piperazine (9.0 g, 38.29 mmol) in ethanol (100 mL) and cyclohexene (7 ml), Pd/C 10% (1.5 g) was added. The mixture was heated at 80° C. for 6 hours until HPLC revealed the disappearance of the starting material. The Pd was filtered from the reaction and the solvents were removed from the filtrate under reduced pressure. The crude was diluted with DCM and treated with HCl in dioxane; the precipitate was collected and washed with diethyl ether to give the final compound as a brown solid in quantitative yield.

1H NMR (400 MHz, DMSO-d₆) δ ppm 2.10 (s, 3H) 2.82 (s, 3H) 2.91-3.01 (m, 2H) 3.06-3.21 (m, 2H) 3.49 (d, J=14.02 Hz, 2H) 3.66 (d, J=12.44 Hz, 2H) 6.57 (bs, 1H) 6.63 (bs, 1H) 7.01 (d, J=7.68 Hz, 1H) 10.21 (bs, 1H)

---

The invention claimed is:

1. A compound of formula (I):

(I)

[chemical structure]

wherein $R_1$ is an optionally substituted group selected from straight or branched $C_1$-$C_3$ alkyl, $C_1$-$C_3$ alkoxy, $C_1$-$C_3$ polyfluorinated alkyl, $C_1$-$C_3$ polyfluorinated alkoxy and —COR' wherein R' is an optionally substituted $C_1$-$C_6$ alkyl;

$R_2$ is a —NR"R'" group wherein R" and R'" are, each independently, hydrogen or an optionally substituted group selected from straight or branched $C_1$-$C_6$ alkyl, $C_3$-$C_6$ cycloalkyl and heterocyclyl or taken together with the nitrogen atom to which they are bonded, R" and R'" may form an optionally substituted heterocyclyl ring optionally containing one additional heteroatom selected from N, O or S;

$R_3$ and $R_4$ are, each independently, hydrogen or an optionally substituted group selected from straight or branched $C_1$-$C_6$ alkyl, $C_3$-$C_6$ cycloalkyl and heterocyclyl, and pharmaceutically acceptable salts thereof, wherein when $R_1$ is $C_1$-$C_3$ alkyl or is alkoxy, R" and R'" are not hydrogen and are not $C_1$-$C_6$ alkyl.

2. A compound of formula (I) as defined in claim 1 wherein:

$R_4$ is an optionally substituted straight or branched $C_1$-$C_6$ alkyl.

3. A compound of formula (I) as defined in claim 1 or 2 wherein:

$R_1$ is a group selected from —OCF$_3$, —OCH$_3$, —CH$_3$ and —COR', wherein R' is as defined in claim 1;

$R_2$ is methylpiperazinyl group

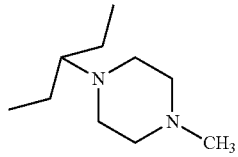

and $R_3$ is $C_3$-$C_6$ cycloalkyl.

4. A compound or a pharmaceutically acceptable salt thereof which is selected from the group consisting of:
- (R)-8-Cyclopentyl-7-ethyl-5-methyl-2-[5-(4-methyl-piperazin-1-yl)-2-trifluoromethoxy-phenylamino]-7,8-dihydro-5H-1-pteridin-6-one,
- (R)-8-Cyclopentyl-7-ethyl-2-[2-methoxy-5-(4-methyl-piperazin-1-yl)-phenylamino]-5-methyl-7,8-dihydro-5H-pteridin-6-one and
- (R)-8-Cyclopentyl-7-ethyl-5-methyl-2-[2-methyl-5-(4-methyl-piperazin-1-yl)-phenylamino]-7,8-dihydro-5H-pteridin-6-one.

5. A process for preparing a compound of formula (I) as defined in claim 1, which process comprises:

St.1) reacting the compound of formula (II):

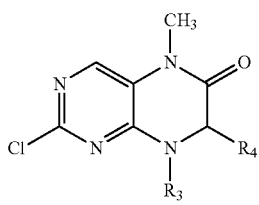

wherein $R_3$ and $R_4$ are as defined in claim 1, with a compound of formula (III):

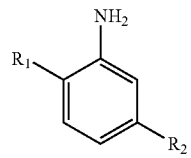

wherein $R_1$ and $R_2$ are as defined in claim 1, to give a compound of formula (I) and optionally converting it into pharmaceutically acceptable salts thereof.

6. A method for treating a disease caused by and/or associated with a dysregulated PLK-1 activity which comprises administering to a mammal in need thereof an effective amount of a compound of formula (I) as defined in claim 1, wherein the disease is selected from the group consisting of colon cancer, breast cancer, ovary cancer, pancreatic cancer and non-small cell lung cancer.

7. The method according to claim 6 further comprising subjecting the mammal in need thereof to a radiation therapy or chemotherapy regimen in combination with at least one cytostatic or cytotoxic agent.

8. The method according to claim 6 wherein the mammal in need thereof is a human.

9. A method for inhibiting the activity of PLK-1 protein which comprises contacting said protein with an effective amount of a compound as defined in claim 1.

10. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

11. A pharmaceutical composition according to claim 10 further comprising one or more chemotherapeutic agents.

12. A product or kit comprising a compound of formula (I) or a pharmaceutically acceptable salt thereof, as defined in claim 1, or pharmaceutical compositions thereof as defined in claim 10 and one or more chemotherapeutic agent, as a combined preparation for simultaneous, separate or sequential use in anticancer therapy.

\* \* \* \* \*